United States Patent
Rutynowski et al.

(10) Patent No.: US 6,206,901 B1
(45) Date of Patent: Mar. 27, 2001

(54) PUNCTURING DEVICE

(76) Inventors: Wlodzimierz Rutynowski, 00-770 Warszawa, ul., Piwarskiego 11/9; Wojciech Wyszogrodzki, 03-289 Warszawa, ul., Ostrodzka 56 X, both of (PL)

( * ) Notice: Subject to any disclaimer, the term of this patent is extended or adjusted under 35 U.S.C. 154(b) by 0 days.

(21) Appl. No.: 09/408,119

(22) Filed: Sep. 29, 1999

(30) Foreign Application Priority Data

Sep. 6, 1999 (PL) .................................................. 335 272

(51) Int. Cl.[7] .................................................. A61B 17/34
(52) U.S. Cl. .................................................. 606/182
(58) Field of Search .................... 606/182, 183; 604/136, 137

(56) References Cited

U.S. PATENT DOCUMENTS

| | | | |
|---|---|---|---|
| 2,092,812 | * 9/1937 | Nemzek | 606/182 |
| 4,139,011 | 2/1979 | Benoit et al. | 128/329 R |
| 4,203,446 | * 5/1980 | Hofert et al. | 606/182 |
| 4,462,405 | * 7/1984 | Ehrlich | 606/182 |
| 4,924,879 | * 5/1990 | O'Brien | 128/770 |
| 5,196,025 | * 3/1993 | Ranalletta et al. | 606/182 |
| 5,356,420 | 10/1994 | Czernecki et al. | 606/182 |
| 5,908,434 | * 6/1999 | Schraga | 606/182 |

FOREIGN PATENT DOCUMENTS

| | | | |
|---|---|---|---|
| 0 694 286 A2 | 1/1996 | (EP) | A61B/5/14 |
| 61-36607 | 3/1986 | (JP) | A61B/5/14 |

* cited by examiner

Primary Examiner—Michael H. Thaler

(57) ABSTRACT

The puncturing device according to the invention comprises the puncturing unit (2) with an exchangeable puncturing insert (7), a driving unit (1) connected with the puncturing unit (2) comprising a ram (12) placed inside the body (9) of the driving unit (1), and at the ram (12) between the first end (13) of the ram (12) pointing towards puncturing insert (7) and the body (9) a driving spring (14) is placed, the second end (17) of the ram (12) is sustained in the body (9), and on the driving unit (1) a triggering unit (3) comprising a button (18) is placed with an inner projection (19) pointing towards the second end (17) of the ram (12).

9 Claims, 2 Drawing Sheets

PUNCTURING DEVICE

FIELD OF THE INVENTION

The object of the present invention is a puncturing device in particular for puncturing skin of a patient in order to take a blood sample for diagnostic purpose.

BACKGROUND OF THE INVENTION

A device for puncturing comprising a sleeve and a pushbutton placed on the one end of the sleeve, is known from U.S. Pat. No. 5,356,420. The second end of the sleeve terminates with a bottom comprising an opening. Inside the sleeve there is a slidably mounted piston, witch at the end closer to the pushbutton is terminated with a pusher, and at end closer to the bottom of the sleeve is terminated with puncturing tip. Inside the sleeve between the end face of the pushbutton and the piston there is placed a driving spring, and between the piston and the bottom of the sleeve there is place a return spring. The piston on the outer circumference has wings resting on inner projection of the sleeve. The U.S. Pat. No. 4,139,011 discloses a device for puncturing skin of a patient comprising a housing in a form of a sleeve with a closed bottom, which, at the other end, is narrowing and has a small opening. Inside the housing there is a slidably mounted rod, which at the one end is terminated with a slider placed inside the opening of the housing. At the other end rod comprises an elastic arm terminated with a holding tooth, which is resting on the edge of the gap in the housing. Between the rod and the bottom a spring is placed and at the other end of a slider a puncturing insert is mounted.

The European patent specification no 0 694 286 describes a device actuating the lancet for puncturing skin of a patient, with a mechanism for pushing out and drawing in a lancet blade. The device comprises a housing with a gap for pushing out a lancet blade. Mechanism actuating comprises a driving spring placed inside the housing, which after being released is pushing out a lancet blade of the gap of the housing, said lancet blade punctures patient's skin and then draws back into the housing.

Japanese patent specification no 61-36607 describes a device for puncturing of the skin, comprising a driving-triggering tubular unit and an attached magazine with a spring, for inserts terminated with a puncturing tip.

SUMMARY OF THE INVENTION

The nature of the puncturing device according to the invention is that the device comprises a puncturing unit with exchangeable puncturing insert, driving unit, connected with puncturing unit, comprising a ram placed inside the body of driving unit, and at the ram between its one end pointing towards puncturing insert, and a body, a driving spring is placed, and the second end of the ram is sustained in the body, and on the driving unit a triggering unit is placed, comprising a button which an inner projection pointing towards the second end of a ram.

Preferably the puncturing unit comprises a housing, with an opening placed at the bottom of said housing and the first return spring situated inside of the said housing.

Preferably exchangeable puncturing insert is placed inside of the housing of puncturing unit. Preferably body of the driving unit comprises inner narrowing in which a ram is placed, moreover said narrowing is a base for a driving spring.

Preferably the body of the driving unit comprises a seating in which the second end of the ram is placed.

Preferably a triggering unit comprises the second return spring placed between the upper edge of the driving unit and the bottom of the button.

BRIEF DESCRIPTION OF THE DRAWINGS

The object of the present invention is presented based on a exemplary embodiment shown in the drawings in which.

DETAILED DESCRIPTION OF THE DRAWINGS

Figures 1, 2:
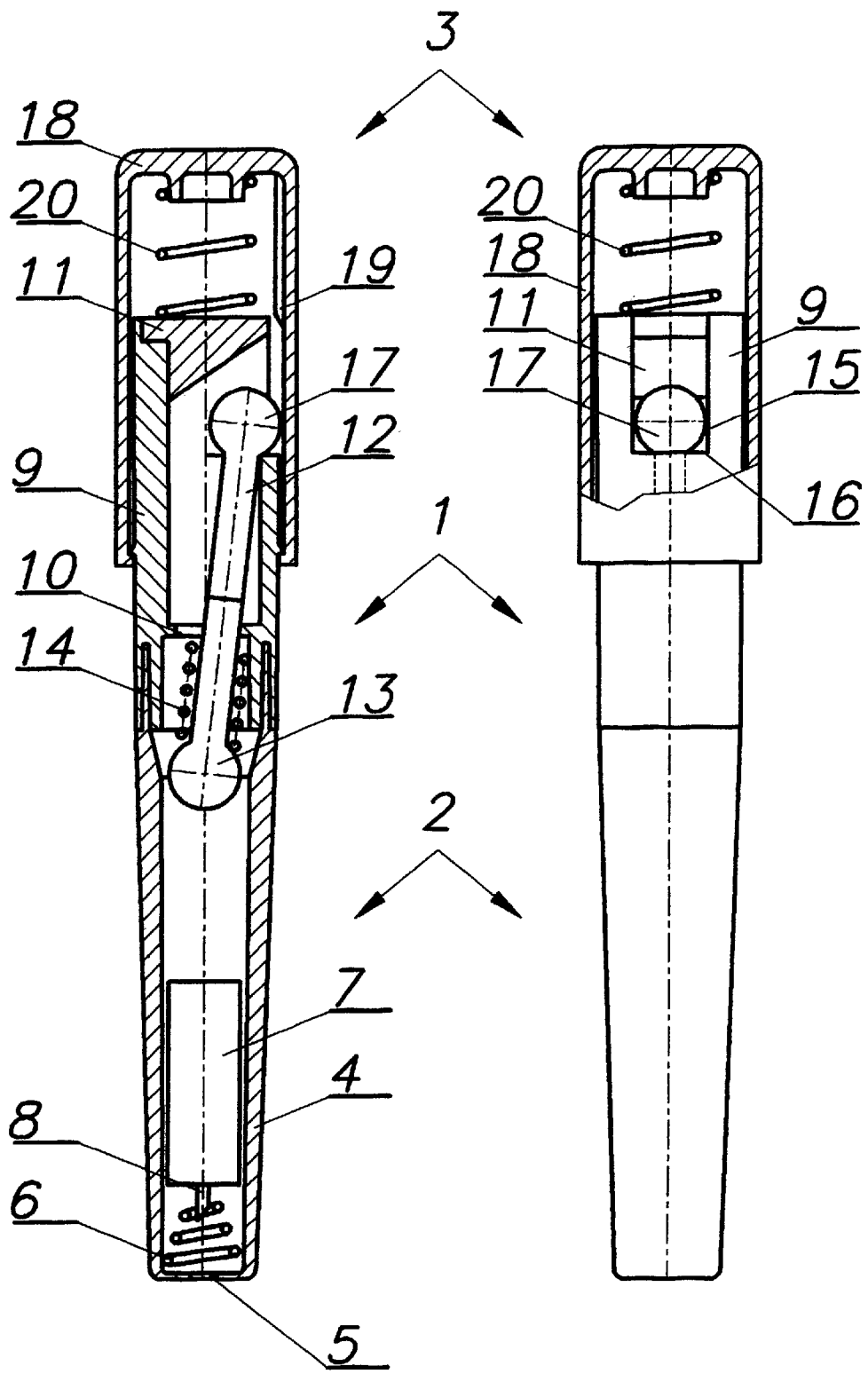
FIG. 1 illustrates the longitudinal section of the puncturing device.
FIG. 2 shows the view of the puncturing device.

As shown in FIGS. 1 and 2, puncturing device comprises a driving unit 1, puncturing unit 2 and triggering unit 3. The puncturing unit 2 includes housing 4, at the bottom of which an opening 5 is placed, inside said housing 4 the first return spring 6 is placed. In the housing 4 of the puncturing unit 2 also an exchangeable puncturing insert 7 with a puncturing needle 8 pointing towards the opening 5 in the bottom of the housing 4 is placed. The driving unit 1, connected with puncturing unit 2, includes the body 9 with inner narrowing 10, which at the one end is open, and at the second end is closed with directing cap 11. In the inner narrowing 10 of the body 9 a ram 12 is placed. At the ram 12 between its one end 13 pointing towards the puncturing insert 7, and the inner narrowing 10, a driving spring 14 is placed. The body 9 includes a seat 15 with the edge 16 supporting the second end 17 of the ram 12. The triggering unit 3 is placed on the driving unit 1 and includes a button 18 with the inner projection 19 pointing towards the second end 17 of the ram 12, and the second return spring 20 is placed between upper edge of the driving unit 1 and the bottom of the button 18.

In order to make a puncture, the puncturing insert 7 is put into the housing 4 of the puncturing unit 2, and then the such prepared puncturing unit 2 is connected with the driving unit 1. After placing a finger to be punctured near opening 5 of the housing 4, the button 18 of the triggering unit 3 is pressed, and an inner projection 19 of the button 18 moving down releases ram 12 of the driving unit 1 by pushing down its second end 17. It results with releasing of the driving spring 14 and the ram with its first end hits the puncturing insert 7. The puncturing needle 8 puncture patient's skin through the opening 5 of the housing 4, then first return spring 6 draws the puncturing insert 7 back into the housing 4 of the puncturing unit 2. After puncturing, the puncturing unit 2 is disconnected from the driving unit 1 and the used puncturing insert 7 is thrown away.

Figure 3:
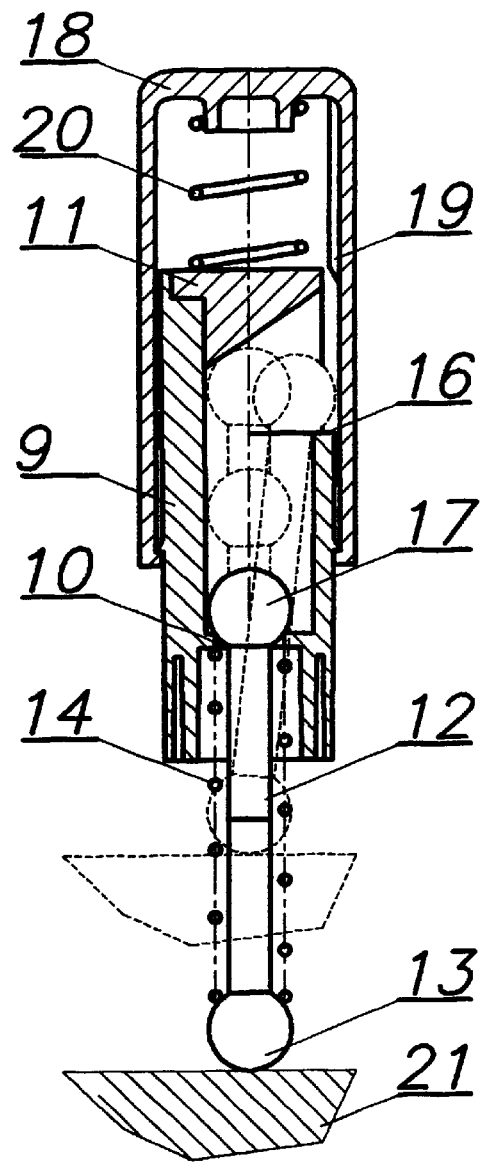
FIG. 3 is a longitudinal section of the driving unit after releasing the ram.

The driving unit after puncturing is in a state shown in FIG. 3. To prepare said driving unit 1 to work, the first end 13 of ram 12 has to be placed against surface 21 and then the driving unit 1 has to be pushed towards said surface. In this way the second end 17 of the ram 12 slides in a directing cap 11 and takes a stable position in a seat 15 of the body 9 resting at the edge 16, and the driving spring 14 is load. After placing next the puncturing insert 7 into the housing 4 of the puncturing unit 2, and placing said puncturing unit 2 onto the driving unit 1, the puncturing device is ready to use.

In a practical embodiment the puncturing device according to the invention may be provided with several marked puncturing units, which geometrical dimensions determine the depth of the puncture.

What is claimed is:

1. A puncturing device, comprising:

a puncturing unit including an exchangeable puncturing insert;

a driving unit, connected to the puncturing unit, comprising a body, a ram disposed within the body, the ram having a first end and a second end, the first end of the ram pointing towards the puncturing insert and the second end of the ram being sustained in the body, and a driving spring surrounding the ram and disposed between the first end of the ram and the second end of the ram; and a triggering unit, mounted on the driving unit, comprising a button and an inner projection pointing towards the second end of the ram, wherein the puncturing unit, the driving unit and the triggering unit are and remain aligned along a common longitudinal axis, and wherein a longitudinal axis of the ram, when the driving spring is loaded, is angled away from said common longitudinal axis and when the driving spring is unloaded, the longitudinal axis of the ram is substantially aligned and coextensive with said common axis.

2. The puncturing device of claim 1, wherein the puncturing unit comprises a housing, an opening disposed at a bottom of said housing, and a first return spring.

3. The puncturing device of claim 2, wherein the exchangeable puncturing insert is disposed inside the housing of the puncturing device.

4. The puncturing device of claim 1, wherein the body of the driving unit comprises an inner narrowing, and wherein said narrowing is a base for the driving spring.

5. The puncturing device of claim 1, wherein the body of the driving unit comprises a seat in which the second end of the ram is placed.

6. The puncturing device of claim 1, wherein the triggering unit comprises a second return spring disposed between an upper end of the driving unit and a bottom of the button.

7. The puncturing device of claim 1, wherein the first end of the ram extends beyond a bottom end of the driving unit when the driving spring is loaded or unloaded.

8. The puncturing device of claim 1, wherein a top end of the driving unit is closed with a directing cap.

9. A puncturing device, comprising:

a puncturing unit including an exchangeable puncturing insert;

a driving unit, connected to the puncturing unit, comprising (i) a body, (ii) a ram having a first end and a second end disposed within the body, wherein in a loaded position a longitudinal axis of the ram is angled away from a longitudinal axis of the driving unit and in an unloaded position the longitudinal axis of the ram is substantially aligned with the longitudinal axis of the driving unit, and (iii) a driving spring surrounding the ram and disposed between the first end of the ram and the second end of the ram; and a triggering unit, mounted on the driving unit, comprising a button and an inner projection pointing towards the second end of the ram, the inner projection pushing the second end of the ram when the button is depressed and the ram is in the loaded position, and wherein a longitudinal axis of the triggering unit is aligned and coextensive with the longitudinal axis of driving unit.

* * * * *